(12) United States Patent
Ohnishi (10) Patent No.: US 8,855,982 B2
(45) Date of Patent: Oct. 7, 2014

(54) ANALYSIS DEVICE AND SIMULATION METHOD

(75) Inventor: Yoshitaka Ohnishi, Kanagawa (JP)

(73) Assignee: Sumitomo Heavy Industries, Ltd., Tokyo (JP)

(*) Notice: Subject to any disclaimer, the term of this patent is extended or adjusted under 35 U.S.C. 154(b) by 313 days.

(21) Appl. No.: 13/366,931

(22) Filed: Feb. 6, 2012

(65) Prior Publication Data

US 2013/0204589 A1 Aug. 8, 2013

(51) Int. Cl.
*G06G 7/48* (2006.01)
*B05C 5/00* (2006.01)
*C03B 37/018* (2006.01)

(52) U.S. Cl.
CPC .............. *C03B 37/018* (2013.01); *B05C 5/00* (2013.01)
USPC ............................................... 703/6

(58) Field of Classification Search
CPC ........ B64C 39/00; G01N 37/00; G06F 15/60; G06F 17/10; G06F 17/18; G06F 17/328; G06F 17/50; G06F 19/00; G06G 7/48; G06G 7/57; G06K 9/00; G06T 15/00; G06T 17/20
USPC ................. 703/1, 2, 6, 8, 9; 345/423; 244/62; 73/28.01; 427/180; 148/692; 65/422; 65/17.4; 428/546; 310/44; 424/9.1; 118/300; 106/64.4; 419/8
See application file for complete search history.

(56) References Cited

U.S. PATENT DOCUMENTS

| | | | | |
|---|---|---|---|---|
| 4,588,443 | A * | 5/1986 | Bache | 106/644 |
| 5,438,526 | A * | 8/1995 | Itoh et al. | 703/2 |
| 5,627,308 | A * | 5/1997 | Dahneke | 73/28.01 |
| 2002/0049572 | A1 * | 4/2002 | Fukuda et al. | 703/2 |
| 2002/0057981 | A1 * | 5/2002 | Park | 419/8 |
| 2005/0017127 | A1 * | 1/2005 | Minh | 244/62 |
| 2005/0114097 | A1 * | 5/2005 | Duncan | 703/1 |
| 2005/0183461 | A1 * | 8/2005 | Kuhn et al. | 65/422 |
| 2008/0115533 | A1 * | 5/2008 | Otsuka et al. | 65/17.4 |
| 2008/0302454 | A1 * | 12/2008 | Kajihara et al. | 148/692 |
| 2009/0056620 | A1 * | 3/2009 | Oda et al. | 118/300 |
| 2009/0213119 | A1 * | 8/2009 | Oh et al. | 345/423 |
| 2010/0088080 | A1 * | 4/2010 | Fitch et al. | 703/6 |
| 2010/0185420 | A1 * | 7/2010 | Ding | 703/2 |
| 2010/0189891 | A1 * | 7/2010 | Usherenko | 427/180 |
| 2010/0303722 | A1 * | 12/2010 | Jin et al. | 424/9.1 |

(Continued)

FOREIGN PATENT DOCUMENTS

| | | |
|---|---|---|
| JP | 10-111880 A | 4/1998 |
| JP | 2000-268064 A | 9/2000 |

(Continued)

OTHER PUBLICATIONS

Japanese Office Action Notification of Reason(s) for Refusal application No. 2011-028218 dated Dec. 3, 2013.

*Primary Examiner* — Kandasamy Thangavelu
(74) *Attorney, Agent, or Firm* — Squire Patton Boggs (US) LLP (57) ABSTRACT

An analysis device that analyzes an object with a predetermined shape is provided which includes a pre-positioned creation unit that creates a system including a plurality of particles, a region specifying unit that specifies a region with the predetermined shape in the system created by the pre-positioned creation unit as a system describing the object, and a numerical calculation unit that numerically calculates a governing equation governing motions of particles in the system describing the object.

5 Claims, 6 Drawing Sheets

(56) References Cited

U.S. PATENT DOCUMENTS

| | | | |
|---|---|---|---|
| 2011/0074231 A1* | 3/2011 | Soderberg | 310/44 |
| 2012/0095738 A1* | 4/2012 | Saito et al. | 703/2 |
| 2013/0089749 A1* | 4/2013 | Slattery | 428/546 |
| 2013/0158965 A1* | 6/2013 | Beckman | 703/6 |
| 2013/0297270 A1* | 11/2013 | Cleary | 703/6 |

FOREIGN PATENT DOCUMENTS

| | | |
|---|---|---|
| JP | 2006-285866 | 10/2006 |
| JP | 2008-040673 A | 2/2008 |
| JP | 2009-037334 | 2/2009 |

* cited by examiner

ANALYSIS DEVICE AND SIMULATION METHOD

BACKGROUND

1. Technical Field

The present invention relates to an analysis device and a simulation method of analyzing a particle system.

2. Description of the Related Art

As a method of finding overall phenomena in material science using a computer on the basis of classical dynamics, quantum mechanics, or the like, simulations based on a molecular dynamics method (Hereinafter, referred to as an "MD method") have been known. The MD method is a limited modeling method because physical properties have potential energy functions applied thereto. However, when the number of particles increases, the complexity dramatically increases and thus only a small number of particles can be treated practically. Therefore, the MD method according to the related art has been often used for applications hardly related to the shape of an analysis object, such as prediction of the physical properties of materials.

Recently, a renormalized molecular dynamics method (hereinafter, referred to as an "RMD method") achieved by developing the MD method so as to treat a macro-scale system has been proposed (for example, see the related art). Thanks to the RMD method, the analysis object has been extended up to macro-scale mechanical structures such as gears or motors.

SUMMARY

According to an embodiment of the present invention, there is provided an analysis device that analyzes an object with a predetermined shape, including: a pre-positioned creation unit that creates a system including a plurality of particles; a region specifying unit that specifies a region with the predetermined shape in the system created by the pre-positioned creation unit as a system describing the object; and a numerical calculation unit that numerically calculates a governing equation governing motions of particles in the system describing the object.

According to another embodiment of the invention, there is provided a simulation method of simulating a mechanical structure with a predetermined shape. The simulation method includes: preparing a system including a plurality of particles and describing a state before the mechanical structure is formed in the predetermined shape; and cutting and analyzing a system with the predetermined shape from the prepared system.

DETAILED DESCRIPTION

When a macro-scale analysis object is treated, it is necessary to set a system reproducing the analysis object including the shape thereof. Accordingly, a method of determining the shape of a system describing an analysis object on the basis of the shape of the analysis object, creating meshes in the shape by the use of mesh creation software, and arranging particles at the grid points of the created meshes has been proposed in the related art. However, in this method, there are cases where particles move to the most stabilized potential positions after the particles are arranged and thus the shape collapses.

The above-mentioned method is often unsuccessful. The inventor proposes the following as the reason.

Regarding a pair potential energy function, the potential energy function depends only on the inter-particle distance and it is not uncommon for this distance to cover third-party neighboring particles. When the inter-particle distance increases, an interaction force becomes smaller. However, since the number of particles interacting with each other increases in proportion to cube of the distance, a situation may occur such that the magnitude of overlapping interaction cannot be ignored.

Due to the influence of overlapping, even when imagining that particles are arranged stably in the initial state, there are often cases that the overall potential energy of the system is not the most stable. Accordingly, the particles move to the most stable positions and depart from the shape to be simulated as a result.

The present applicant suggests a solution to such a problem in the related art. The related art discloses that the potential energy function between particles should be corrected. That is, it enables performing simulation without collapsing the shape by setting the initial distance between the grid points arranged by the use of the mesh creation software so as to stabilize the potential energy function.

However, the correction of the potential energy function may cause an undesirable situation. Therefore, there is a need for another solution applicable to more situations.

It is desirable to provide an analysis technique capable of creating a more stable system as a system describing an object having a predetermined shape.

According to this embodiment, it is possible to create a system describing an object from a system including plural particles.

Arbitrary combinations of the above-mentioned constituent elements or mutual substitutions of the constituent elements or expressions of embodiments of the present invention among a device, a method, a system, a computer program, and a recording medium storing the computer program are effective as embodiments of the present invention.

Hereinafter, an exemplary embodiment of the present invention will be described with reference to the accompanying drawings. The same or equivalent constituent elements, members, and processes shown in the drawings will be referenced by the same reference signs and description thereof will not be repeated.

When a macro-scale object having a predetermined shape such as a gear, a beam, or a motor is described and analyzed using a system including plural particles, it is necessary to stabilize the particles at positions based on the shape of the object but it is difficult to arrange the particles at the most stable positions in the initial state as described above. Therefore, in an analysis device according to this embodiment, the particles are not arranged in the shape of the object from the first time, but a particle system (hereinafter, referred to as an ingot particle system) sufficiently larger than a particle system to be created is prepared, a relaxation calculation is performed thereon, and then a target shape is cut out from the result. Accordingly, without correcting the potential energy function described in the related art, it is possible to create a stable complex shape through the use of a plain particle method such as an MD method and an RMD method.

Figure 1:
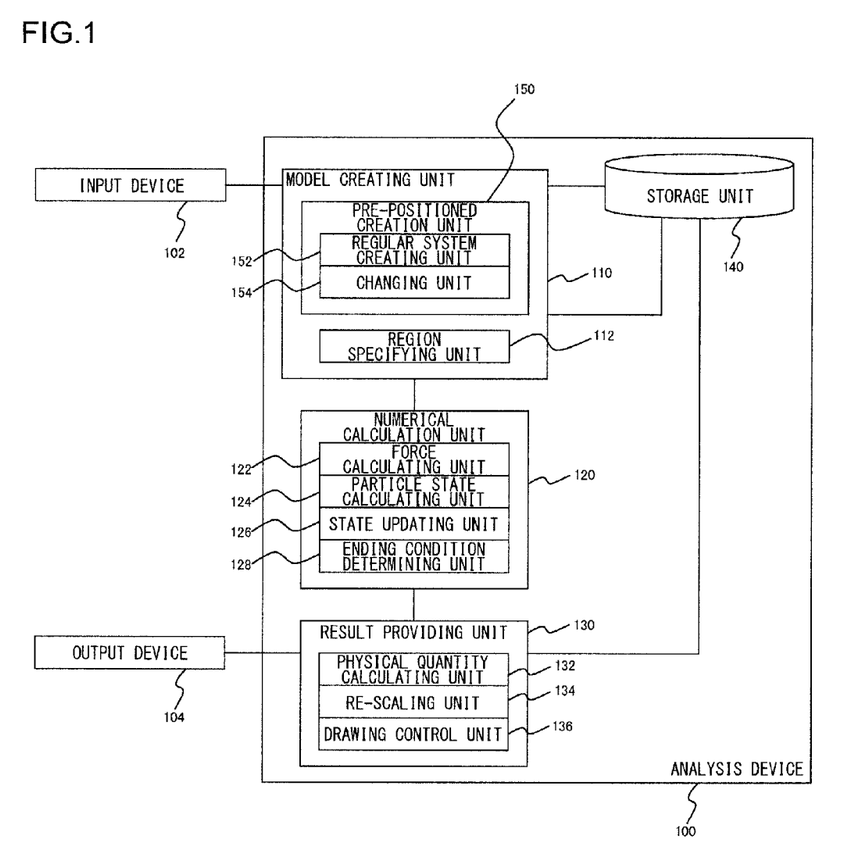
FIG. 1 is a block diagram illustrating the functions and configuration of an analysis device according to an embodiment of the present invention.

FIG. 1 is a block diagram illustrating the functions and configuration of an analysis device 100. The blocks shown in the drawing may be embodied by elements such as a CPU (Central Processing Unit) of a computer or mechanical devices in hardware or may be embodied by a computer program in software, but functional blocks embodied in cooperation therewith are shown herein. Therefore, it will be easily understood by those skilled in the art that the functional blocks can be embodied in various forms depending on the combination of hardware and software.

The analysis device 100 describes an object having a predetermined shape through the use of a system including plural particles and analyzes the system by numerically calculating an equation of motion of the particles. The analysis device 100 acquires the temporal development or static state of the system by the calculation, and simulates the object or provides predicted values of physical quantities of the object by the use of the acquired data.

In this embodiment, an example where a particle system is analyzed through the use of an MD method or an RMD method will be described, but it will be obvious to those skilled in the art and reading this specification that the technical concept of this embodiment can be applicable to an example where a particle system is analyzed through the use of other particle methods such as a DEM (Distinct Element Method), an SPH (Smoothed Particle Hydrodynamics), and an MPS (Moving Particle Semi-implicit).

The analysis device 100 is connected to an input device 102 and an output device 104. The input device 102 may include a keyboard or a mouse used to receive a user's input associated with the processes performed by the analysis device 100. The input device 102 may be constructed to receive an input from a network such as the Internet or a recording medium such as a CD or a DVD. The output device 104 may include a display machine such as a display or a printing machine such as a printer.

The analysis device 100 includes a model creating unit 110, a numerical calculation unit 120, a result providing unit 130, and a storage unit 140.

The model creating unit 110 creates a particle system S including N (where N is a natural number) particles and describing an object from an ingot particle system SI on the basis of input information acquired from a user through the use of the input device 102. The model creating unit 110 stores a position, an initial velocity, and a mass of each particle in the created particle system S as initial conditions of the particle system S in the storage unit 140.

When the MD method is used, the particles may be made to correspond to atoms or molecules. Alternatively, when the RMD method is used, the particles may be set as particles in a renormalized system.

The model creating unit 110 includes a pre-positioned creation unit 150 and a region specifying unit 112.

The pre-positioned creation unit 150 creates an ingot particle system SI including M (where M is a natural number larger than N) particles and being larger than the particle system S to be created. The ingot particle system SI may be, for example, a regular system in which particles are regularly arranged, or an amorphous system in which particles are arranged in an amorphous shape, or a polycrystalline system in which particles are arranged to exhibit a polycrystalline state.

Figure 2:
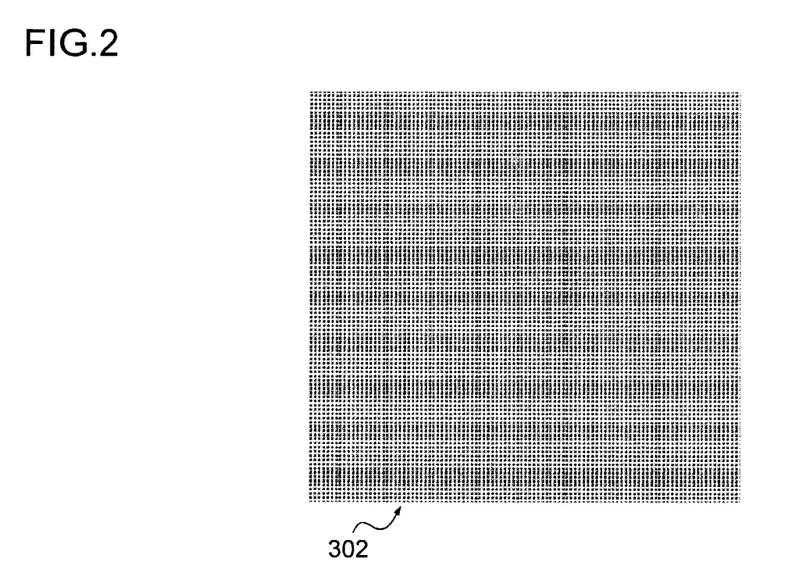
FIG. 2 is a diagram schematically illustrating a regular system.

FIG. 2 is a diagram schematically illustrating a regular system 302. In the regular system 302 shown in FIG. 2, particles are arranged in a face-centered cubic lattice shape. Therefore, by keeping the temperature of the regular system 302 low, it is possible to maintain the regular system 302 in a state close to a single-crystal state without collapsing the crystal.

Figure 3:
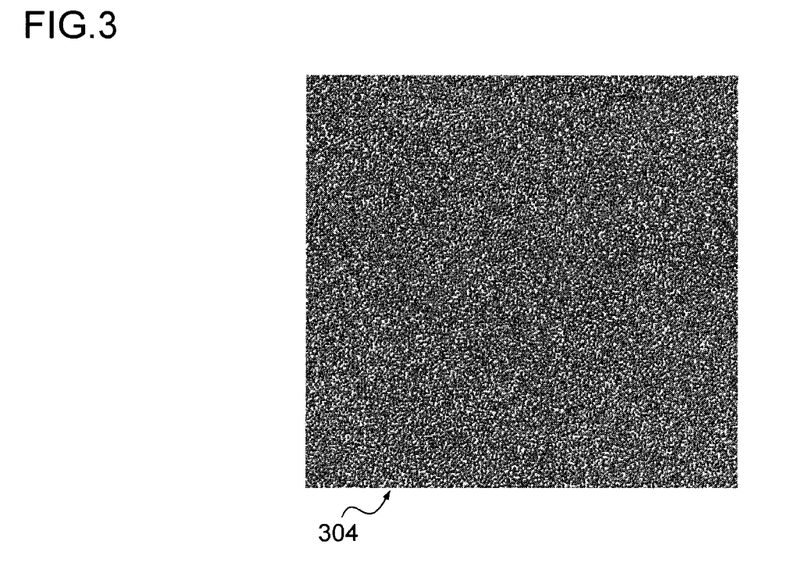
FIG. 3 is a diagram schematically illustrating an amorphous system.

FIG. 3 is a diagram schematically illustrating an amorphous system 304. The amorphous system 304 is obtained, for example, by first creating a regular system, temporarily raising the temperature of the regular system, and then rapidly cooling the regular system.

Figure 4:
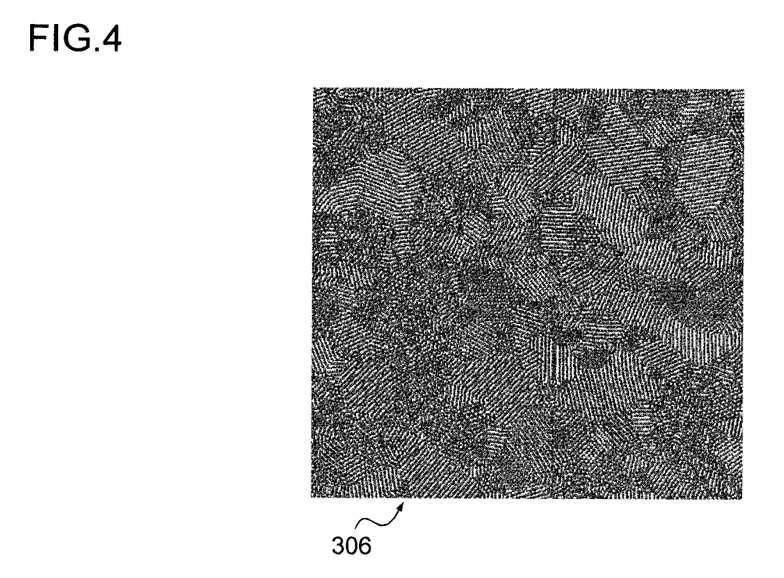
FIG. 4 is a diagram schematically illustrating a polycrystalline system.

FIG. 4 is a diagram schematically illustrating a polycrystalline system 306. The polycrystalline system 306 is obtained, for example, by first creating a regular system, temporarily raising the temperature of the regular system, and then slowly cooling the regular system.

In the polycrystalline system, as shown in FIG. 4, since a state where microcrystals of a polycrystal have different crystal axes are reproduced, the polycrystalline system exhibits non-uniformity in comparison with a regular system or an amorphous system exhibiting uniformity.

FIG. 1 is referred to again.

The pre-positioned creation unit 150 includes a regular system creating unit 152 and a changing unit 154.

The regular system creating unit 152 creates a regular system including M particles and larger than the particle system S to be created. Particularly, the regular system created by the regular system creating unit 152 has such a size that the particle system S does not depart from the regular system.

The regular system creating unit 152 sets a region larger than a region to be occupied by the particle system S in a virtual three-dimensional space and arranges M particles in the region so as to have a regular structure. This regular structure may be a predetermined crystal structures such as a face-centered cubic lattice structure, a body-centered cubic lattice structure, and a hexagonal close-packed structure, or may be meshes created through the use of a known mesh creating technique.

The changing unit 154 changes the regular system created by the regular system creating unit 152 on the basis of a governing equation governing motions of particles in the regular system. Particularly, the changing unit 154 changes the regular system to a system which is more stable in potential than the regular system, such as an amorphous system or a polycrystalline system. The system which is more stable in potential than the regular system can be said to be a system in which a spontaneous change has progressed more than the regular system. Alternatively, the system which is more stable in potential than the regular system can be said to be a system in which more time has passed than the regular system.

For example, the changing unit 154 gives the regular system created by the regular system creating unit 152 as an input to the numerical calculation unit 120 to be described later along with a predetermined relaxation calculation condition such as a change in temperature. The numerical calculation unit 120 performs repeated calculation using discretized equations of motions of particles with the state of the regular system created by the regular system creating unit 152 as an initial state. When the calculation is sufficiently repeated by the numerical calculation unit 120 to reach a static state or the like, the changing unit 154 acquires information of the system obtained through the repeated calculation as information of the changed system from the numerical calculation unit 120. That is, the changing unit 154 acquires information of the system relaxed with the elapse of sufficient time from the initial state as information of the changed system.

For example, when the predetermined relaxation calculation condition is set to a condition of temporarily raising the temperature of the system and then rapidly cooling the system in the repeated calculation of the numerical calculation unit 120, an amorphous system can be obtained as the changed system. For example, when the predetermined relaxation calculation condition is set to a condition of temporarily raising the temperature of the system and then slowly cooling the system in the repeated calculation of the numerical calculation unit 120, a polycrystalline system can be obtained as the changed system.

The changing unit 154 may change the regular system created by the regular system creating unit 152 on the basis of the equations of motion of particles in the regular system. Alternatively, the changing unit 154 may transmit the information of the regular system created by the regular system creating unit 152 to an external calculation device (not shown) and may acquire information of the calculation result of the external calculation device based on the equations of motion of particles in the regular system as the information of the changed system from the external calculation device.

The pre-positioned creation unit 150 creates the regular system created by the regular system creating unit 152 or the system changed by the changing unit 154 as the ingot particle system SI.

The region specifying unit 112 acquires information of the shape of an object from input information. The region specifying unit 112 specifies a region having the acquired shape of an object as the particle system S in the ingot particle system SI created by the pre-positioned creation unit 150.

Figure 5:
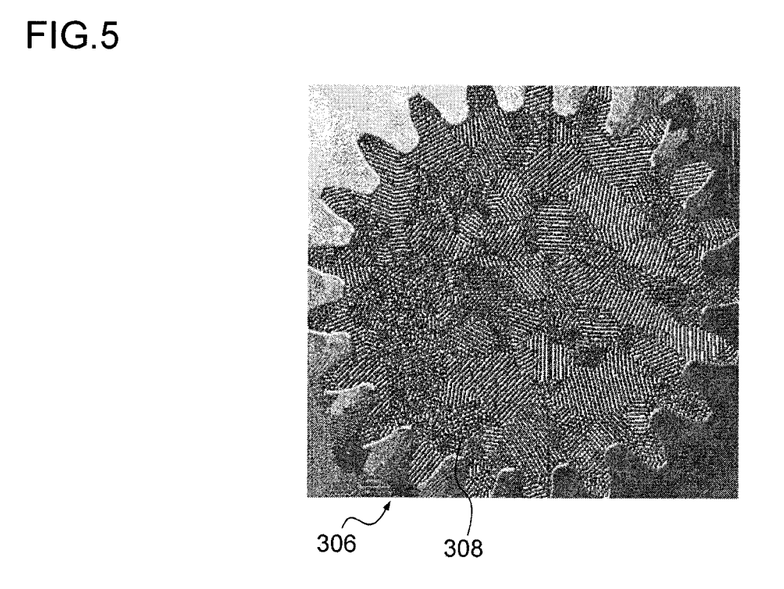
FIG. 5 is a diagram schematically illustrating a region specified in the polycrystalline system shown in FIG. 4 by a region specifying unit shown in FIG. 1.

FIG. 5 is a diagram schematically illustrating a region 308 specified in the polycrystalline system 306 shown in FIG. 4 by the region specifying unit 112. The object is an involute spur gear and thus the region specifying unit 112 specifies the region 308 having the shape of the spur gear in the polycrystalline system 306.

Figure 6:
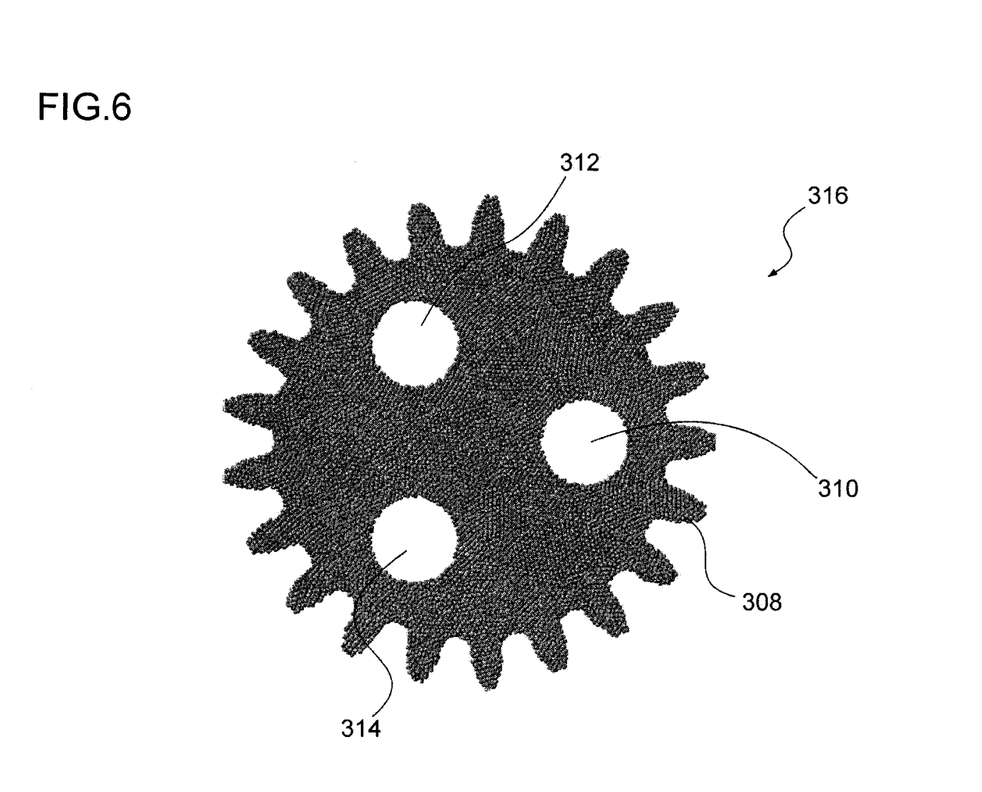
FIG. 6 is a diagram schematically illustrating a particle system created by incorporating a rigid body into the specified region shown in FIG. 5.

The region specifying unit 112 may perform a predetermined process on the specified region for the purpose of facilitating subsequent calculation. FIG. 6 is a diagram schematically illustrating a particle system 316 created by incorporating rigid bodies 310, 312, and 314 into the specified region 308 shown in FIG. 5. The rigid bodies 310, 312, and 314 are provided to add an external force for rotation of the particle system 316.

FIG. 1 is referred to again.

It is assumed in the below description that the particles in the particle system S are set to be homogeneous or equivalent to each other and the potential energy function is a pair potential function and has the same without depending on the particles. However, it will be apparent to those skilled in the art and reading this specification that the technical concept of this embodiment is applicable to other cases.

The numerical calculation unit 120 numerically calculates a governing equation governing the motions of particles in a system for the particle system S created by the model creating unit 110 and the regular system created by the regular system creating unit 152 in some cases. Particularly, the numerical calculation unit 120 performs repeated calculation based on the discretized equations of motion of the particles. The numerical calculation unit 120 includes a force calculating unit 122, a particle state calculating unit 124, a state updating unit 126, and an ending condition determining unit 128.

The force calculating unit 122 calculates a force acting on each particle in the particle system S on the basis of inter-particle distances with reference to information of the particle system S stored in the storage unit 140. The force calculating unit 122 determines particles (hereinafter, referred to as neighboring particles) to which the distance from the i-th particle ($1 \leq i \leq N$) in the particle system S is smaller than a predetermined cutoff distance. The force calculating unit 122 calculates the force of each neighboring particle acting on the i-th particle on the basis of the potential energy function between the neighboring particle and the i-th particle and the distance between the neighboring particle and the i-th particle. Particularly, the force calculating unit 122 calculates the force from the value of the gradient of the potential energy function with the value of the distance between the corresponding neighboring particle and the i-th particle. The force calculating unit 122 calculates the force acting on the i-th particle by summing the forces of all the neighboring particles acting on the i-th particle.

The particle state calculating unit 124 calculates at least one of the position and the velocity of each particle by applying the force calculated by the force calculating unit 122 to the discretized equations of motion of the particles for each particle in the particle system S with reference to the information of the particle system S stored in the storage unit 140. In this embodiment, the particle state calculating unit 124 calculates both the position and the velocity of each particle.

The particle state calculating unit 124 calculates the velocity of each particle from the discretized equations of motion of particles including the force calculated by the force calculating unit 122. The particle state calculating unit 124 calculates the velocity of each particle by substituting the force calculated by the force calculating unit 122 for the equations of motion of particles discretized with a predetermined minute time interval $\Delta t$ by the use of a predetermined numerical analysis method such as a leapfrog method or an Euler method for the i-th particle in the particle system S. The velocity of each particle calculated in the previous repeated calculation is used in this calculation.

The particle state calculating unit 124 calculates the position of each particle on the basis of the calculated velocity of each particle. The particle state calculating unit 124 calculates the position of each particle by applying the calculated velocity of each particle to a relational expression of the positions and the velocities of the particles discretized with the time interval $\Delta t$ by the use of a predetermined numerical analysis method for the i-th particle in the particle system S. The position of each particle calculated in the previous repeated calculation is used in this calculation.

The state updating unit 126 updates the positions and velocities of the particles in the particle system S stored in the storage unit 140 to the positions and velocities calculated by the particle state calculating unit 124.

The ending condition determining unit 128 determines whether the repeated calculation of the numerical calculation unit 120 should be ended. Examples of the ending condition for ending the repeated calculation include a condition that the repeated calculation is performed a predetermined number of times, a condition that the particle system S reaches a static state, and a condition that an ending instruction is received from the outside. The ending condition determining unit 128 ends the repeated calculation of the numerical calculation unit 120 when the ending condition is satisfied. The ending condition determining unit 128 returns the flow of processes to the force calculating unit 122 when the ending condition is not satisfied. Then, the force calculating unit 122 calculates the force at the position of each particle updated by the state updating unit 126 again.

The result providing unit 130 provides a user with the analysis result of the particle system S created by the model creating unit 110. The result providing unit 130 includes a physical quantity calculating unit 132, a rescaling unit 134, and a drawing control unit 136.

The physical quantity calculating unit 132 calculates various physical quantities such as temperature, pressure, and stress of the particle system S on the basis of the information of the particle system S stored in the storage unit 140, after the repeated calculation of the numerical calculation unit 120 is ended.

When the particles in the particle system S are changed particles in a renormalized system by the model creating unit 110, the rescaling unit 134 converts the physical quantities calculated by the physical quantity calculating unit 132 into the physical quantities of the non-renormalized system. The particularly, the rescaling unit 134 acquires the physical quantities of the non-renormalized system by multiplying the physical quantities calculated by the physical quantity calculating unit 132 by a scaling factor determined for each physical quantity. The physical quantities include physical quantities invariable with the renormalization conversion, such as stress or temperature. 1 (invariable before and after the conversion) is set as the scaling factor for such physical quantities. The rescaling unit 134 causes the output device 104 to display the converted physical quantities.

The drawing control unit 136 causes the output device 104 to graphically display the temporal development or the static state of the particle system S on the basis of the information of the positions and velocities of the particles in the particle system S stored in the storage unit 140, after the repeated calculation of the force calculating unit 122 is ended.

In the above-mentioned embodiment, examples of the storage unit 140 include a hard disk and a memory. On the basis of the description of this specification, it will be understood by those skilled in the art reading this specification that the respective units can embodied by a CPU not shown, a module of an application program installed therein, a module of a system program, a memory temporarily storing the details of data read from the hard disk, or the like.

The operation of the analysis device 100 having the above-mentioned configuration will be described.

Figure 7:
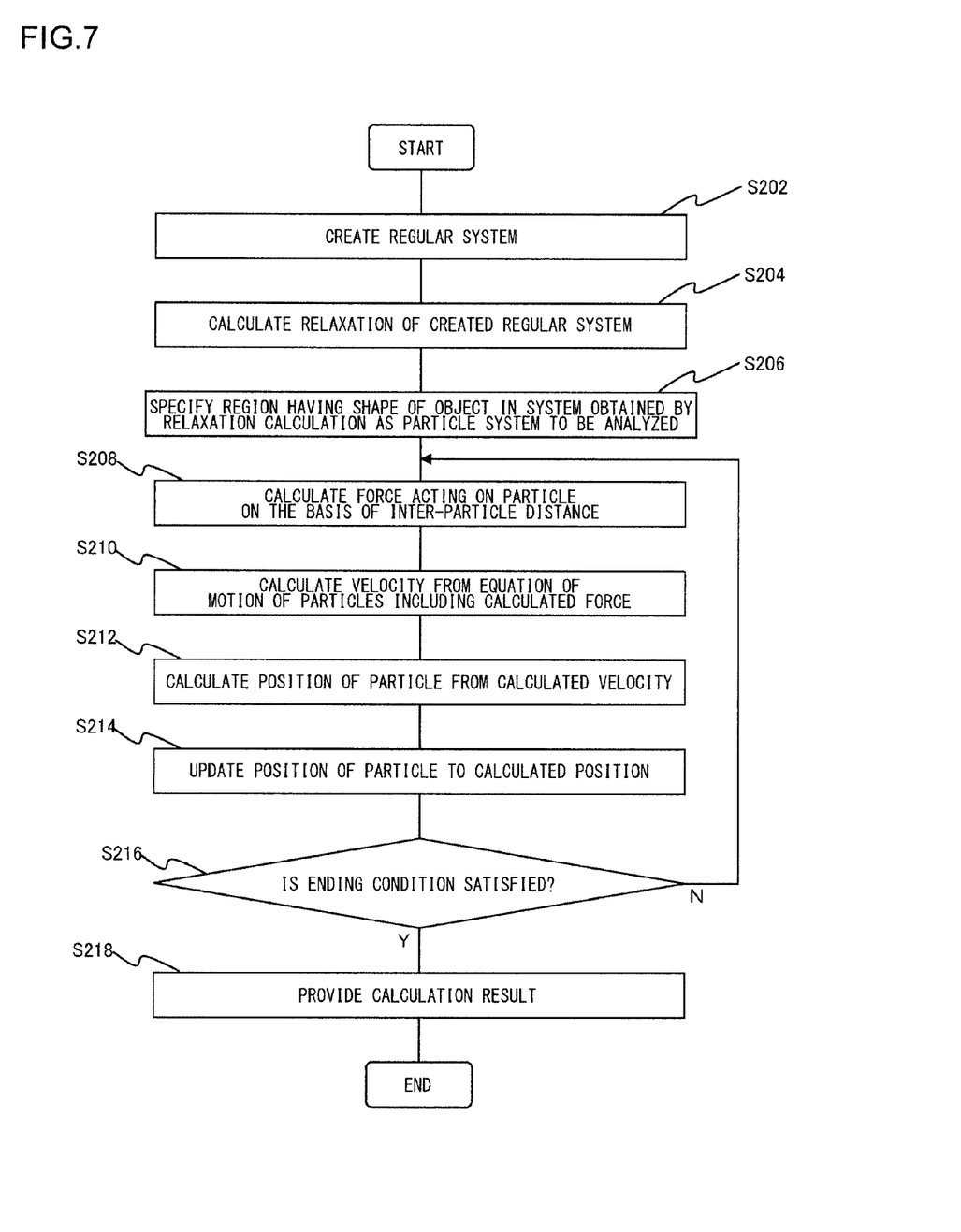
FIG. 7 is a flowchart illustrating an example of a flow of processes in the analysis device shown in FIG. 1.

FIG. 7 is a flowchart illustrating an example of a series of processes in the analysis device 100. The regular system creating unit 152 creates a regular system (S202). The changing unit 154 causes the numerical calculation unit 120 to perform the relaxation calculation of the created regular system (S204). The region specifying unit 112 specifies a region having the shape of an object in the system acquired as the relaxation calculation as a particle system to be analyzed (S206). The force calculating unit 122 calculates the forces acting on the particles from the inter-particle distances (S208). The particle state calculating unit 124 calculates the velocities from the equations of motion of particles including the calculated forces (S210). The particle state calculating unit 124 calculates the positions of particles from the calculated velocities (S212). The state updating unit 126 updates the positions of particles stored in the storage unit 140 to the calculated position (S214). The ending condition determining unit 128 determines whether an ending condition is satisfied (S216). When it is determined that the ending condition is not satisfied (N in S216), the flow of processes is returned to step S208. When it is determined that the ending condition is satisfied (Y in S216), the result providing unit 130 provides a user with the calculation result.

In the analysis device 100 according to this embodiment, the ingot particle system SI larger than the particle system S is first created and the region as the particle system S is specified in the ingot particle system SI. Accordingly, it is possible to reduce an unexpected variation in shape of the particle system S due to movement of particles in the numerical calculation on the particle system S.

In the analysis device 100 according to this embodiment, when the region specifying unit 112 creates the particle system S in the system changed by the changing unit 154, the system changed by the changing unit 154, that is, the ingot particle system SI, can be made into a system having been subjected to sufficient relaxation calculation. Such a system is, for example, the amorphous system 304 shown in FIG. 3 or the polycrystalline system shown in FIG. 4. In this case, since the particles are the most stabilized in potential or move to positions close to the most stabilized positions through the relaxation calculation, most particles in the particle system S cut out of the ingot particle system SI are the most stabilized in potential or are located at the positions close to the most stabilized positions. Therefore, unexpected movement of particles due to such a tendency that the overall system is the most stabilized in potential is limited in the numerical calculation of the particle system S, and the variation in shape due to the movement is suppressed. As a result, it is possible to create a particle system S which is further stabilized in potential.

For example, in the analysis device 100 according to this embodiment, by incorporating a "pattern" shown in FIG. 5 into the polycrystalline system 306 shown in FIG. 4 to prune extra particles, the particle system 316 having a complex shape shown in FIG. 6 is obtained. As the result of the inventor's study, since the particles included in the particle system 316 created in this way are almost located at the stabilized positions in potential, slight surface reconstruction has been observed but such movement of particles to collapse the shape has not been observed.

In the analysis device 100 according to this embodiment, when the changing unit 154 changes the regular system created by the regular system creating unit 152 to a system having non-uniformity such as a polycrystalline system and the region specifying unit 112 cuts out the particle system S from the system having non-uniformity, it is possible to more naturally introduce non-uniformity into the particle system S. In general, many metals or ceramics are polycrystalline bodies and can thus be analyzed by the analysis device 100, but often have non-uniformity. In the analysis device 100 according to this embodiment, since it is possible to create a particle system S including the non-uniformity, it is possible to achieve more suitable simulation.

In the method according to the related art of determining the shape of a particle system and then arranging particles therein, since it is difficult even to maintain the shape of the particle system as described above, it is unrealistic to introduce non-uniformity into the particle system from the first time. On the contrary, in the analysis device 100 according to this embodiment, it is possible to further naturally introduce the non-uniformity into the particle system.

In the analysis device 100 according to this embodiment, various ingot particle systems SI such as the amorphous system 304 shown in FIG. 3 and the polycrystalline system 306 shown in FIG. 4 can be created depending on the relaxation calculation conditions. A mechanical structure such as a gear is actually often formed in a predetermined shape through the use of a cutting work or the like on a base metal. In the analysis device 100 according to this embodiment, an ingot particle system SI describing the state before the mechanical structure is formed in a predetermined shape can be created when simulating the mechanical structure. For example, the analysis device 100 can create a polycrystalline system describing a base metal. In the analysis device 100, by cutting out a particle system S having a predetermined shape from the ingot particle system SI prepared in this way and analyzing the cut particle system, it is possible to create a particle system S which is more stable in shape and to enable realistic simulation suitable for an object.

Figure 8:
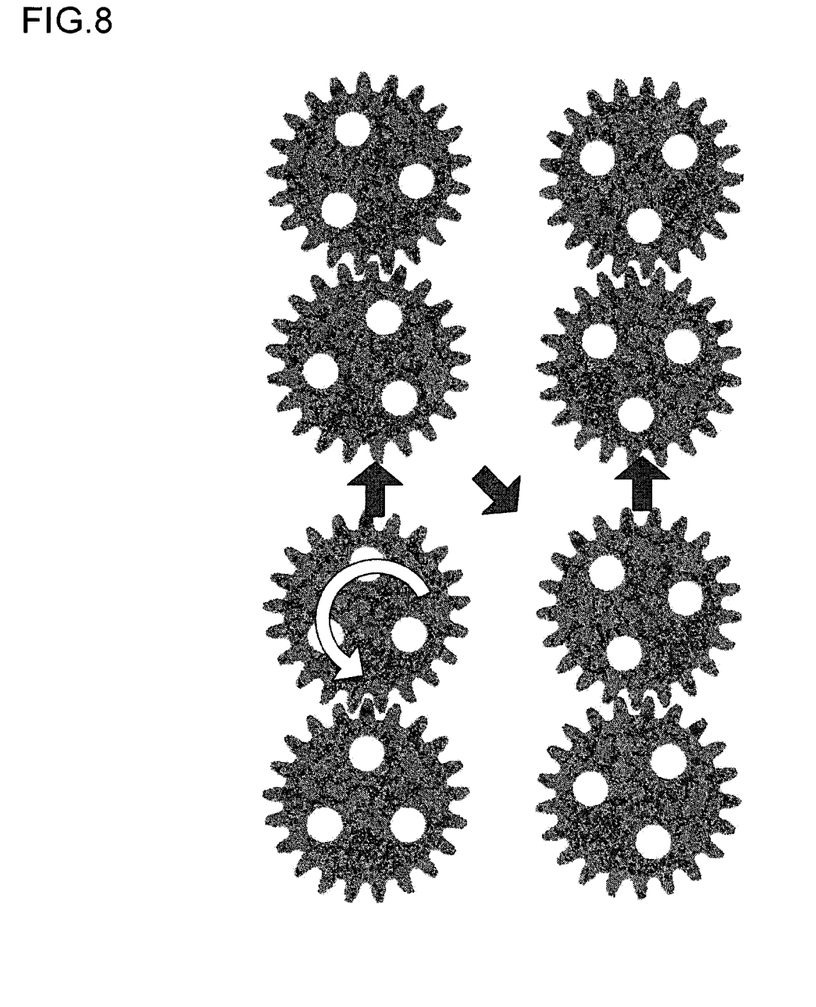
FIG. 8 is a diagram schematically illustrating the result of dynamic analysis using two particle systems being shown in FIG. 6 and describing an involute spur gear.

FIG. 8 is a diagram schematically illustrating the result of dynamic analysis using two particle systems shown in FIG. 6 and describing an involute spur gear. The gray scale in FIG. 8 represents the magnitude of stress. The black arrow represents the elapse of time. The white arrow represents that the right side (input side) of two spur gears rotates. The left gear passively rotates with the rotation of the right gear.

From this result, it can be seen that the stress in the polycrystalline grain boundary is great. This result corresponds to the knowledge that a skidding along a grain boundary can easily occur in the polycrystalline system. Therefore, in the analysis device 100 according to this embodiment, it is possible to further realistically evaluate a fatigue or breakdown phenomenon of an object.

The inventor considers that it is not necessary to create a system having a complex shape in the MD method, but the method of creating a system having a complex shape becomes more important with an extension in applicable range of the RMD method in the future. The analysis device 100 according to this embodiment can create a system having a complex shape and being stable in a natural manner and can thus suitably cope with such a situation.

The configuration and operation of the analysis device 100 according to this embodiment have been described above. It will be easily understood by those skilled in the art that the embodiment is only an example, various modifications can be made in combinations of the constituent elements or processes, and the modifications belong to the scope of the invention.

It should be understood that the invention is not limited to the above-described embodiment, but may be modified into various forms on the basis of the spirit of the invention. Additionally, the modifications are included in the scope of the invention.

What is claimed is:

1. An analysis device that analyzes an object with a predetermined shape, comprising:
    a computer with a processor and a memory;
    a pre-positioned creation unit that creates, using the processor, an ingot particle system, larger than a particle system describing the object, and including a plurality of particles, wherein a relaxation calculation is performed, using the processor, for the plurality of particles included in the ingot particle system;
    a region specifying unit that specifies, using the processor, a region with the predetermined shape in the ingot particle system created by the pre-positioned creation unit as the particle system describing the object; and
    a numerical calculation unit that numerically calculates, using the processor, a governing equation governing motions of particles in the particle system describing the object.

2. The analysis device according to claim 1, wherein the pre-positioned creation unit includes
    a regular system creating unit that creates a system including a plurality of particles regularly arranged as the ingot particle system, and
    a changing unit that changes the ingot particle system created by the regular system creating unit to the ingot particle system on which the relaxation calculation is performed, on the basis of the governing equation governing the motions of particles in the system, and
    wherein the region specifying unit specifies the region with the predetermined shape in the ingot particle system changed by the changing unit.

3. The analysis device according to claim 2, wherein the changing unit changes the ingot particle system created by the regular system creating unit so as to cause the plurality of particles included in the ingot particle system to exhibit non-uniformity.

4. A simulation method of simulating a mechanical structure with a predetermined shape, comprising:
    preparing, using a processor, an ingot particle system including a plurality of particles, describing a state before the mechanical structure is formed in the predetermined shape, and larger than a particle system describing the mechanical structure;
    creating, using the processor, the ingot particle system on which a relaxation calculation is performed for the plurality of particles included in the ingot particle system; and
    cutting and analyzing, using the processor, a particle system with the predetermined shape from the created ingot particle system.

5. A non-transitory computer-readable medium, said computer-readable medium containing computer code which, when run on a computer, causes the computer to execute a process of analyzing an object with a predetermined shape, the process comprising:
    creating an ingot particle system larger than a particle system describing the object and including a plurality of particles on which a relaxation calculation is performed;
    specifying a region with the predetermined shape in the ingot particle system created as the particle system describing the object; and
    numerically calculating a governing equation governing motions of particles in the particle system describing the object.

* * * * *